United States Patent
Ghashghaeinia (10) Patent No.: US 10,420,746 B2
(45) Date of Patent: Sep. 24, 2019

(54) PHARMACEUTICAL COMPOSITION CONTAINING BAY 11-7082, PARTHENOLIDE OR A COMBINATION THEREOF FOR THE TREATMENT OF OBESITY OR CARDIOVASCULAR DISEASES

(71) Applicant: Mehrdad Ghashghaeinia, Stuttgart (DE)

(72) Inventor: Mehrdad Ghashghaeinia, Stuttgart (DE)

(73) Assignee: Mehrdad Ghashghaeinia, Stuttgart (DE)

( * ) Notice: Subject to any disclaimer, the term of this patent is extended or adjusted under 35 U.S.C. 154(b) by 0 days.

(21) Appl. No.: 15/958,307

(22) Filed: Apr. 20, 2018

(65) Prior Publication Data

US 2018/0235922 A1     Aug. 23, 2018

Related U.S. Application Data

(63) Continuation of application No. PCT/EP2016/075416, filed on Oct. 21, 2016.

(30) Foreign Application Priority Data

Oct. 21, 2015 (DE) .......................... 10 2015 117882

(51) Int. Cl.
    *A61K 31/277*     (2006.01)
    *A61K 31/225*     (2006.01)
    *A61K 31/365*     (2006.01)
    *A61P 3/04*     (2006.01)
    *A61P 9/04*     (2006.01)
    *A61K 45/06*     (2006.01)

(52) U.S. Cl.
    CPC .......... *A61K 31/277* (2013.01); *A61K 31/225* (2013.01); *A61K 31/365* (2013.01); *A61K 45/06* (2013.01); *A61P 3/04* (2018.01); *A61P 9/04* (2018.01); *A61K 2300/00* (2013.01)

(58) Field of Classification Search
    CPC ............................... A61K 31/277; A61P 3/04
    USPC ........................................................ 514/468
    See application file for complete search history.

(56) References Cited

U.S. PATENT DOCUMENTS 6,953,787 B2 * 10/2005 Smith ................... C07D 223/16
                                                514/212.02
2004/0054001 A1    3/2004 Joshi et al.

FOREIGN PATENT DOCUMENTS

| | | |
|---|---|---|
| JP | 2009126801 A | 6/2009 |
| KR | 20120032372 A | 4/2012 |
| WO | WO-02/055067 A2 | 7/2002 |
| WO | WO-2005/023241 A1 | 3/2005 |
| WO | WO-2012/145678 A1 | 10/2012 |
| WO | WO-2015/042294 A1 | 3/2015 |

OTHER PUBLICATIONS

German patent application No. 10 2015 117 882.6, Office Action, dated Aug. 25, 2016.
Ghashghaeinia et al., Pharmacological targeting of glucose-6-phosphate dehydrogenase in human erythrocytes by Bay 11-7082, parthenolide and dimethyl fumarate, Sci. Rep., 6:28754 (Jun. 2016).
Ghashghaeinia et al., Roles of the NFκB and glutathione pathways in mature human erythrocytes, Cellular & Molecular Biology Letters, 17(1):11-20 (2012).
Gupta et al., Inhibition of NF-kappaB induces regression of cardiac hypertrophy, independent of blood pressure control, in spontaneously hypertensive rats, Am. J. Physiol. Heart Circ. Physiol., 289(1):H20-9 (2005).
International Application No. PCT/EP2016/075416, International Search Report and Written Opinion (English translation), dated Feb. 15, 2017.
Kim et al., BAY 11-7082, a nuclear factor-?B inhibitor, reduces inflammation and apoptosis in a rat cardiac ischemia-reperfusion injury model, Int. Heart J., 51(5):348-53 (2010).
Shin et al., Catechin gallates are NADP+-competitive inhibitors of glucose-6-phosphate dehydrogenase and other enzymes that employ NADP+ as a coenzyme, Bioorg. Med. Chem., 16(7):3580-6 (2008).
Cong et al., "Cardiac-specific overexpression of catalase prevents diabetes-induced pathological changes by inhibiting NF-κb signaling activation in the heart," *J. Mol. Cell Cardiol.*, 89(Pt. B):314-25 (2015).
Liu et al., "Nuclear factor-κb inhibition improves myocardial contractility in rats with cirrhotic cardiomyopathy," *Liver Int.*, 28(5):640-8 (2008).

* cited by examiner

*Primary Examiner* — Kevin E Weddington
(74) *Attorney, Agent, or Firm* — Marshall, Gerstein & Borun LLP (57) ABSTRACT

The present invention relates to the treatment and/or prophylaxis of obesity and/or an NADPH superoxide anion ($O_2.^-$) associated cardiovascular disease.

8 Claims, 7 Drawing Sheets

PHARMACEUTICAL COMPOSITION CONTAINING BAY 11-7082, PARTHENOLIDE OR A COMBINATION THEREOF FOR THE TREATMENT OF OBESITY OR CARDIOVASCULAR DISEASES

CROSSREFERENCES TO RELATED APPLICATIONS

This application is a continuation of copending international patent application PCT/EP2016/075416 filed on 21 Oct. 2016 and designating the U.S., which has been published in German, and claims priority from German patent application DE 10 2015 117 882.6 filed on 21 Oct. 2015. The entire contents of these prior applications are incorporated herein by reference.

FIELD

The present invention relates to the treatment and/or prophylaxis of obesity and/or an NADPH superoxide anion ($O_2.^-$) associated cardiovascular disease.

BACKGROUND

Obesity is a nutritional and metabolic disease connected with massive overweight, which is characterized by an above-normal increase of body fat causing pathological effects. Obesity frequently appears in industrialized countries, in particular under living conditions which are characterized by little physical activity and at the same time by an abundance of food. The main reasons are overeating and lack of exercise, socio-cultural and genetic factors. Obesity may occur as the result of other diseases such as metabolic diseases. Obesity is also described as a consequence of adverse reactions to medicinal products or as caused by prenatal factors, the food quality or the sleep habits.

The current therapy is largely restricted to a sustainable change of the eating behavior and physical activity, the use of psychotherapy as well as the inclusion of the partners and family.

Nevertheless, in particular in the industrialized countries still an increase of obesity can be observed. For this reason there is a need for new therapeutic approaches and in particular medicinal products by means of which obesity can be prevented or treated in a targeted manner.

People with heart failures or cardiac insufficiencies, respectively, have an extremely high activity of the NADPH-dependent oxygenase (NOX). Under these conditions this hyperactive enzyme produces large amounts of superoxide anion molecules ($O_2.^-$). ($O_2.^-$) as well as other harmful forms of oxygen are summarized by the term "reactive oxygen species" (ROS). This enduring increase of the intracellular ($O_2.^-$) results in a growth of the oxidative stress in the cardiac muscle cells of the affected patients. This causes an apoptosis of the cardiac muscle cells.

The currently used medicinal products of choice for the treatment of NADPH superoxide anion associated cardiovascular diseases, such as the congestive cardiac insufficiency, are ACE blockers, AT1 antagonists, beta blockers, diuretics, aldosterone antagonists or cardiac glycosides.

Despite of intensive researches the congestive cardiac insufficiency is one of the most common internal diseases with an estimated number of more than 100 millions of affected people in Europe. Cardiac insufficiency is one of the most frequent consultation issues in Germany in the general medical practice and the most common reason for a stationary hospital admission.

For this reason there is a need for new therapeutic concepts and medicinal products by means of which NADPH superoxide anion associated cardiovascular diseases can be prevented or treated in a targeted manner.

SUMMARY

Against this background it is a problem underlying the invention to provide a method for the treatment and/or prophylaxis of obesity and/or an NADPH superoxide anion associated cardiovascular disease, which allows a targeted intervention into the metabolism of these diseases and which offers to affected patients an alternative or an additional medicinal treatment option over the current ones.

This problem is solved by administering into a living being in need one or more active agents selected from the group consisting of Bay 11-7082, parthenolide and dimethylfumarate (DMF).

Bay 11-7082 (CAS 19542-67-7) or (E)-3-[(4-methylphenylsulfonyl]-2-propene¬nitrile; 3-[(4-methylphenyl)sulfonyl]-(2E)-propenenitrile, having a molecular weight of 207.25 g/mol and a molecular formula of $C_{10}H_9NO_2S$ is described in the literature as a potential anti-inflammatory agent. Bay 11-7082 has also been associated with the stimulation of stress-activated protein kinases, p38 and JNK-1.

Parthenolide (CAS 20554-84-1) is also referred to as (1aR,7aS,10aS,10bS)-1a,5-dimethyl-8-methylene-2,3,6,7,7a,8,10a,10b-octahydrooxireno[9,10]cyclodeca[1,2-b]furane-9(1aH)-on and has a molecular weight of 248.32 g/mol and a molecular formula of $C_{15}H_{20}O_3$. Parthenolide is a sesquiterpenlactone which can be found in feverfew, a plant species of the composite flower family. A variety of biological activities is described for parthenolide, such as the modulation of the NF-kappaB mediated inflammatory responses in experimental arteriosclerosis and the induction of apoptosis in AML cells, but also an activity against the parasites *Leishmania amazonensis*.

Dimethylfumarate (CAS 624-49-7), also referred to as (E)-2-butenedioic acid dimethyl ester or fumeric acid dimethyl ester, molecular weight of 144.13 g/mol, molecular formula of $C_6H_8O_4$, is described for the treatment of multiple sclerosis, psoriasis or other chronic skin and autoimmune diseases. The WO 2010/003528 proposes dimethylfumarate for the treatment of parasites of the species *Plasmodium falciparum* and *Plasmodium berghei*.

The active agents according to the invention have so far not been associated with the treatment and/or prophylaxis of obesity or NADPH superoxide anion associated cardiovascular diseases. Therefore, the findings of the inventor was surprising and not to be expected.

It is understood that the active agents may be comprised by a pharmaceutical composition. The latter may comprise a pharmaceutically acceptable formulation. Pharmaceutically acceptable formulations are well-known in the state of the art. By the way of example, it is referred to Kibbe A. (2003), Handbook of Pharmaceutical Excipients, 4th edition, American Pharmaceutical Association and Pharmaceutical Press. The pharmaceutical composition according to the invention can also contain additives. They include any compound or composition which are advantageous for the use according to the invention and include salts, binders, solvents, dispersing agents and further compounds which are usually used in connection with the formulation of medicinal products.

The composition according to the invention may be available in any type of administration, such as an injection or drinkable solution, capsule, tablet, pill, ointment, lotion, gel, paste etc.

To achieve a systemic circulation of the composition according to the invention, in particular such containing DMF, in particular with obese patients, venous blood can be withdrawn from the affected individual, and transferred into a blood bag within which the composition according to the invention has been pre-deposed. Once a certain amount of time has passed, the so-treated blood is fed back to the individual. This treated blood can now systemically circulate in the body of the individual and can reach many organs within seconds, including the fatty tissue with its brown and white cells and the liver with its hepatocytes. The liver is the main site of the fat biosynthesis. Thus, white fat cells of the fatty tissue (WATs=white adipocytes tissue) which store large amounts of energy, can be converted into the brown and energy-consuming fat cells (BATs=brown adipocytes tissue). Hence, the patient can lose weight in a natural way by increased energy consumption. Furthermore, the molecules (Bay 11-7082, parthenolide and dimethylfumarate) in the blood plasma can reach the liver cells within a few seconds and can keep in check their G6PDH mediated fatty acid biosynthesis. In addition, the erythrocytes in their function as drug transporters loaded with dimethylfumarate, parthenolide or Bay 11-7082 can directly give their load (dimethylfumarate, parthenolide and Bay 11-7082) to the liver cells and, in doing so, can restrict and negatively influence the activity of the liver cells and the fatty acid biosynthesis by inhibition of G6PDH. By this particular approach the problem described for DMF is addressed, which hardly circulates systemically after oral application; Dibbert S. et al. 2013; Arch Dermatol Res. 305: 447-451.

According to the invention each of the proposed active agents may be administered as the sole active agent, and may therefore be configured as monotherapeutic component. However, in an alternative embodiment, two or three of the proposed active agents or even further active agents may be co-administered.

According to a preferred embodiment of the invention the administration or treatment with the pharmaceutical composition results in an inhibition of the glucose-6-phosphate dehydrogenase (G6PDH).

The inventor has surprisingly realized that all of the three substances are specific inhibitors of the G6PDH. This characteristic which was realized for the first time results in the advantage of the invention that an enzyme is addressed which is described in the literature as an effective therapeutic target for a variety of metabolic diseases. Here it is of particular advantage that the three active agents, already in low concentrations, result in a complete (Bay 11-7082, parthenolide) or a 50% inhibition of G6PDH. This inhibitory potential in respect of the G6PDH can hardly be found in the state of the art; see Shin et al. (2008), "Catechin gallates are $NADP^+$-competitive inhibitors of glucose-6-phosphate dehydrogenase and other enzymes that employ $NADP^+$ as a coenzyme", Bioorganic & Medicinal Chemistry 16, pages 3580-3586. The authors have selected from three million commercially available substances in a "virtual screening experiment" 250 potential substances which were promising in regards of their inhibitory effect on the G6PDH activity. Only 8 substances thereof were in the position to inhibit at clinically relevant concentrations more than 50% of the activity of G6PDH.

Individuals which suffer from obesity or NADPH superoxide anion associated cardiovascular diseases have something in common: the enzyme G6PDH has an extremely high activity. The NADPH producing enzyme G6PDH by itself is inhibited by NADPH. To escape from an NADPH depending G6PDH inhibition and, at the same time, to produce further NADPH molecules the cells take advantage of the protein HSCARG; see Barcia-Vieitez R. & Ramos-Martínez J. I. 2014, IUBMB Life 66: 775-779. This protein scavanges excess NADPH molecules and may contribute significantly to the fatty acid biosynthesis as "NADPH-charged HSCARG" by subsequent and controlled release of the NADPH molecules. This mechanism is the reason why the high G6PDH activity is maintained despite a very high NADPH concentration. In this way the development of obesity or NADPH superoxide anion associated cardiovascular diseases is substantially fostered.

This deficiency in G6PDH inhibition can be compensated by the invention.

According to an embodiment of the invention the active agent is administered in such a concentration which results in vivo in a ≥50%, preferably ≥60%, further preferably ≥70%, further preferably ≥80%, further preferably ≥90%, highly preferably ≥100% inhibition of the G6PDH.

This measure has the advantage that selectively such an inhibition of the G6PDH is effected which is required for the optimum treatment or prophylaxis of obesity or the NADPH superoxide anion associated cardiovascular disease.

According to an embodiment the active agent is administered in such a concentration that in vivo the following concentration is achieved:

approximately ≥1, preferably approximately ≥5, further preferably approximately ≥0, further preferably approximately ≥15, further preferably approximately ≥20 µM Bay 11-7082, and/or approximately ≥1, preferably approximately ≥0, further preferably approximately ≥20, further preferably approximately ≥30, further preferably approximately ≥40, further preferably approximately ≥50 µM parthenolide, and/or approximately ≥10, preferably approximately ≥20, further preferably approximately ≥40, further preferably approximately ≥60, further preferably approximately ≥100, further preferably approximately ≥140 µM DMF.

This measure has the advantage that such concentrations of the active agent are used which, according to the findings of the inventor, will achieve a maximum inhibition of the G6PDH. For this reason the administration or the pharmaceutical composition is especially effective in the treatment or prophylaxis of obesity or the NADPH superoxide anion associated cardiovascular disease.

According to an embodiment of the invention the administration or treatment with the pharmaceutical composition results in an inhibition of the glutathione reductase (GR).

As the inventor could surprisingly realize Bay 11-7082 completely and DMF by 50% also inhibit the enzyme GR. This has the advantage that another enzyme is addressed which is involved in the metabolism of obesity and NADPH superoxide anion associated cardiovascular diseases. This characteristic of the active agent according to the invention results in an especially high effectivity of the pharmaceutical composition by synergistic effects due to the simultaneous inhibition of G6PDH and GR.

According to an embodiment of the invention the active agent is administered in such a concentration that in vivo an inhibition of the GR is achieved by ≥50%, preferably ≥60%, further preferably ≥70%, further preferably ≥80%, further preferably ≥90%, highly preferably ≥100%.

This measure has the advantage that selectively such an inhibition of the GR is achieved which in each of the individual to be treated causes optimum results. In this context it is of particular advantage that Bay 11-7082 and DMF result in a maximum inhibition of the GSR at the same concentrations in vivo which also result in a maximum inhibition of G6PDH. This simplifies the formulation of the pharmaceutical composition according to the invention to a significant degree and reduces side effects.

According to a preferred embodiment of the invention the NADPH superoxide anion associated cardiovascular disease is congestive cardiac insufficiency.

This measure has the advantage that one of the most important forms of the NADPH superoxide anion associated cardiovascular diseases is prevented or therapeutically addressed in a targeted manner.

Another subject-matter of the present invention relates to the use of Bay 11-7082, parthenolide and dimethylfumarate (DMF) for the treatment and/or prophylaxis of obesity and/or an NADPH superoxide anion ($O_2.^-$) associated cardiovascular disease.

The features, characteristics, and advantages of the method and the pharmaceutical composition according to the invention apply correspondingly to the use according to the invention.

Another subject-matter of the present invention relates to a method for the treatment and/or prophylaxis of obesity and/or an NADPH superoxide anion ($O_2.^-$) associated cardiovascular disease comprising the administration of one or more active agents into a living being in need, which are selected from the group consisting of: Bay 11-7082, parthenolide and dimethylfumarate (DMF).

It will be understood that the afore-mentioned features and those to be described hereinafter cannot only be used in the respectively given combination, but also in different combinations or independently, without departing from the scope of the present invention.

The invention is now explained in more detail by means of embodiments which result in further features, characteristics, and advantages. The embodiments are purely illustrative and do not restrict the scope of the invention. It is understood that characteristics which are described in connection with a specific embodiment are isolated characteristics of the invention in its general form and do not only apply in the specific technical context.

EXAMPLES

1. Material and Methods 1.1 Erythrocytes

Highly pure erythrocyte concentrates with defined cellular composition of healthy volunteers, virtually free of white blood cells (WBCs) containing less than 1 permille thrombocytes, were obtained from the blood bank of the University of Tübingen. The study on human erythrocytes was approved by the Ethics Committee of the University of Tübingen (343/2008BO2). Aliquots of the individual erythrocyte concentrates were either used directly at 0.4% or 0.6% hematocrit (Hct) or stored at 4° C. for up to a week.

1.2 Solutions and Chemicals

For the in vitro experiments on suicidal death of erythrocytes (0.4% Hct), the determination of the glutathione content and the measurement of the enzyme activities (0.6% Hct), the incubations were carried out in Ringer solution in a total volume of 2, 30, or 13 ml, respectively. The Ringer solutions contain (in mM): 125 NaCl, 5 KCl, 1.2 $MgSO_4$, 32 N-2-hydroxyethylpiperazine-N'-2-ethane sulfonic acid (HEPES)/NaOH (pH 7.4), 5 glucose, and 1 $CaCl_2$. The annexin-binding buffer contained (in mM): 125 NaCl, 10 HEPES/NaOH (pH 7.4), and 5 $CaCl_2$. Where indicated Bay 11-7082 (1-20 μM), parthenolide (1-50 μM) and dimethylfumarate (1-140 μM) were added. DMSO served as solvent and DMSO-treated erythrocytes as negative controls (0.2% (v/v) DMSO). Bay 11 7082, parthenolide, dimethylfumarate (DMF), N-ethylmaleimide (NEM), glutathione reductase (GR) and GSSG were purchased from Sigma (Taufkirchen, Germany). Annexin V-FLUOS was purchased from Roche Diagnostics (Mannheim, Germany).

1.3 Flow Cytometry

Erythrocyte concentrates (0.4% Hct), suspended in 2 ml Ringer solution were treated in the absence or presence of Bay 11-7082, parthenolide or DMF for 24 and 48 hours. After the incubation, 0.1 ml erythrocytes ($2 \times 10^6$ RBCs) were washed in 500 μl annexin-binding buffer. The erythrocyte's pellets were then vortexed gently to get a homogenous cell suspension. To detect the exposure of phosphatidylserine (PS) on the outer leaflet of the plasma membrane, these cells were subsequently stained with 32 μl annexin-V-FLUOS at a 1:33 dilution and mixed gently on a vortex mixer. After 20 minutes of incubation in the dark at room temperature, 200 μl of annexin-binding buffer was given to each sample, thoroughly vortexed to achieve single-cell suspensions and analyzed by flow cytometry on a FACS Calibur (Becton Dickinson, Heidelberg, Germany). The cell volume differences were determined by forward scatter (FSC), and annexin-V-FLUOS-binding was measured in the FL1 channel.

1.4 Hemolysis

The erythrocytes concentrates (0.4% Hct) were treated with varying concentrations of Bay 11-7082, parthenolide and DMF for 24 hours and 48 hours, then the hemolysis was determined. Briefly, after the incubation 600 µl (1.2×10$^7$ RBCs) of each condition were centrifuged for 4 minutes at 420×g and 4° C., and the supernatants were harvested. To quantify the hemolysis, the hemoglobin concentration of the supernatant was determined photometrically at 405 nm. The absorption of the supernatant of erythrocytes lysed in distilled water was defined as 100% hemolysis.

1.5 Intracellular Measurements of Glutathione (GSH and GSSG) via HPLC

Erythrocyte concentrates (0.6% Hct), suspended in 30 ml of Ringer solution were treated with varying concentrations of Bay 11-7082, parthenolide, and DMF for 24 hours. DMSO-treated erythrocytes served as negative controls. After the incubation the erythrocytes were treated with 0.6 mM (final concentration) of N-ethylmaleimide prepared as a 310 mM stock solution in H$_2$O. After an incubation for 2 minutes at room temperature the samples were centrifuged at 210×g for 10 minutes in order to obtain RBC pellets. These were immediately stored at −20° C. until GSH and GSSG analyses were performed. All measurements were carried out within one week after the treatment.

GSH and GSSG were measured in the clear supernatant obtained by the treatment of 0.1 ml RBCs with 0.12 ml (15% w/v) trichloroacetic acid. The GSH analysis was carried out by HPLC. Briefly, one aliquot (0.05 ml) of the supernatant was loaded onto the HPLC and the GS-NEM conjugate was revealed by a diode-array detector at 265 nm. The GSSG was measured photometrically by the GSH recycling method with slight modifications. For the determination of hemoglobin, one aliquot of RBCs (10 µl) was hemolyzed by 1:200 dilution with H2O hemolyzed. The HPLC analyses were carried out with an Agilent series 1100 instrument. The photometric analyses were performed with a Jasco V-530 instrument.

1.6 Enzyme Measurement

The erythrocyte concentrates (0.6% hematocrit), suspended in 13 ml Ringer solution were treated with varying concentrations of Bay 11-7082, parthenolide, and DMF for 24 hours. DMSO-treated erythrocytes served as negative controls. The determination of the enzymatic activity (G6PDH, 6PGDH and GR (±FAD) was performed in leukocytes and platelet-free erythrocytes lysates according to standard biochemical procedures. After 10 minutes of incubation (20 minutes for GR) at 37° C. the reaction was started by adding substrate of co-factor. Changes in the absorbance at 340 nm were recorded at 1 minute intervals for 20 minutes (Infinite 200 Nanoquant spectrophotometer). The specific activity of all enzymes was expressed as U/g Hb. The combined activity of G6PDH and 6PGDH was determined by estimating the conversion of NADP$^+$ to NADPH in the presence of glucose-6-phosphate. The activity of 6PGDH alone was then measured by the conversion of NADP to NADPH in the presence of 6-phosphogluconate. Finally, the G6PDH activity was then calculated by deducing the 6PGDH-activity from the total dehydrogenase activity.

2. Results 2.1 Effect of Bay 11-7082, Parthenolide and Dimethylfumarate on the Reduced Form of the Antioxidants Glutathione (GSH)

A single mature human erythrocyte contains 3×10$^8$ GSH molecules, thus 1 µl of human blood with approximately ≥5×10$^6$ erythrocytes contains approximately ≥1.5×10$^{15}$ GSH molecules. In this experiment 6 µl (approximately ≥3×10$^7$) erythrocytes per ml of Ringer solution were used (0.6% Hct). The total number of the GSH molecules in these erythrocytes were therefore approximately ≥0.9×10$^{16}$.

In the same 1 ml of Ringer solution with 20 µM Bay 11-7082 the number of the Bay 11 7082-molecules was exactly 1.2×10$^{16}$. With the same principle the number of the parthenolide molecules with 50 µM parthenolide per ml of Ringer solution was exactly 3×10$^{16}$ and the number of the dimethylfumarate molecules with 140 µM dimethylfumarate per 1 ml of Ringer solution was exactly 8.4×10$^{16}$. Thus, there were the following molar ratios for Bay 11-7082 to GSH (1.3), parthenolide to GSH (3.3), and dimethylfumarate to GSH (9.3).

Each and every one of the pharmacological substances Bay 11-7082, parthenolide and dimethylfumarate is in a position in a ratio of 1:1 to irreversibly and directly bind the reduced form of the glutathione (GSH) and, in doing so, to deplete the latter. As a result, these substances in the used experimental system could bind all GSH molecules and, at the same time, could exist in the erythrocytes as free and non-bound Bay 11-7082, parthenolide, and dimethylfumarate molecules.

Furthermore, a significant part of the GSH molecules in mammalian cells but also in non-nucleated erythrocytes binds to a variety of proteins. This process is known as glutathionylation. Thus, in the applied experimental system the share in the free and not-bound Bay 11-7082, parthenolide and dimethylfumarate molecules must be much higher than shown by the above ratios. Therefore it has been assumed that in the used experimental system concentrations of 20 µM Bay 11-7082, 50 µM parthenolide or 140 µM dimethylfumarate cause an entire GSH depletion.

Figure 1:
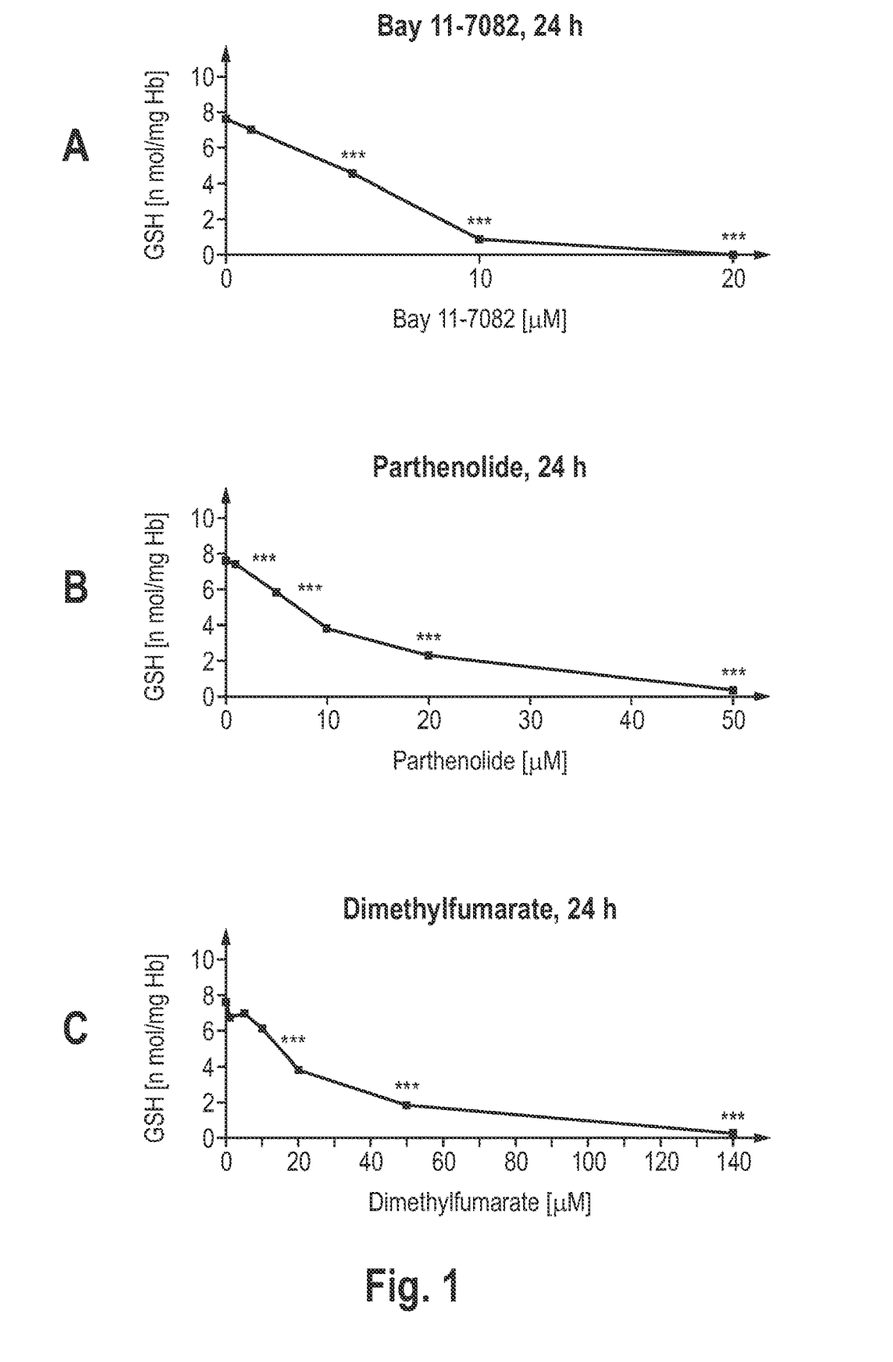
FIG. 1 measurement of the depletion of glutathione (GSH) in mature human erythrocytes caused by Bay 11-7082, parthenolide and dimethylfumarate, by means of the HPLC technology.

The corresponding result is shown in the FIG. 1. Human erythrocytes (0.6% Hct) were treated for 24 hours in presence and absence of Bay 11-7082, parthenolide or dimethylfumarate. The experiment was carried out for three times in total with blood from different individuals.

This approach (the presence of a molar excess of the non-bound and free molecules of Bay 11-7082, parthenolide, or dimethylfumarate) resulted in the planning of further experiments to examine a potential influence of these substances on the redox relevant enzymes such as glucose-6-phosphate dehydrogenase (G6PDH), 6-phosphogluconolactone dehydrogenase (6PGDH) and glutathione reductase (GR) in human erythrocytes.

2.2 Depletion Effect of Bay 11-7082, Parthenolide or Dimethylfumarate on the Oxidized Form of the Glutathione (GSSG) and Their Inhibitory Effect on the Activity of the Glucose-6-Phosphate Dehydrogenase (G6PDH).

Several dozen commercially available pro-oxidative substances as well as many biological/physiological molecules existing in natural cells, such as hydrogen peroxide (H$_2$O$_2$), shift the intracellulary existing high GSH/GSSG ratio on the principle of a so-called inverse correlation in favor of a high GSSG/GSH ratio. These (dynamic) reciprocal proportionality between intracellular GSH and GSSG concentrations loses its validity if the cells are treated with the pharmacological substances Bay 11-7082, parthenolide or dimethylfumarate.

The GSH depletion caused by these substances, which results in no increase but in a decrease of the intracellular GSSG concentration (see table 1), forces the affected cells both to produce more GSH but also to convert the present GSSG molecules into GSH. As a result, the redox capacity of the cell is maintained. For the reversible conversion of GSSG into GSH the cell uses the very effective, highly specific and antiapoptotic G6PDH-NADPH-GR system; see FIG. 2.

TABLE 1

Treatment of human erythrocytes with Bay 11-7082, parthenolide or dimethylfumarate is associated with a factual complete GSSG depletion. Human erythrocytes (0.6% Hct) were treated for 24 hours in absence or presence of Bay 11-7082, parthenolide or dimethylfumarate. These substances were solved in dimethyl sulfoxide (DMSO) and the DMSO-treated erythrocytes served as negative control. Number of the independent experiments n = 3.

|  | DMSO | Bay 11-7082 (20 μM) | Parthenolide (50 μM) | Dimethylfumarate (140 μM) |
| --- | --- | --- | --- | --- |
| GSSG [nmol/mg Hemoglobin] | 0.06 | 0.03 | 0.03 | 0.03 |

Figure 2:
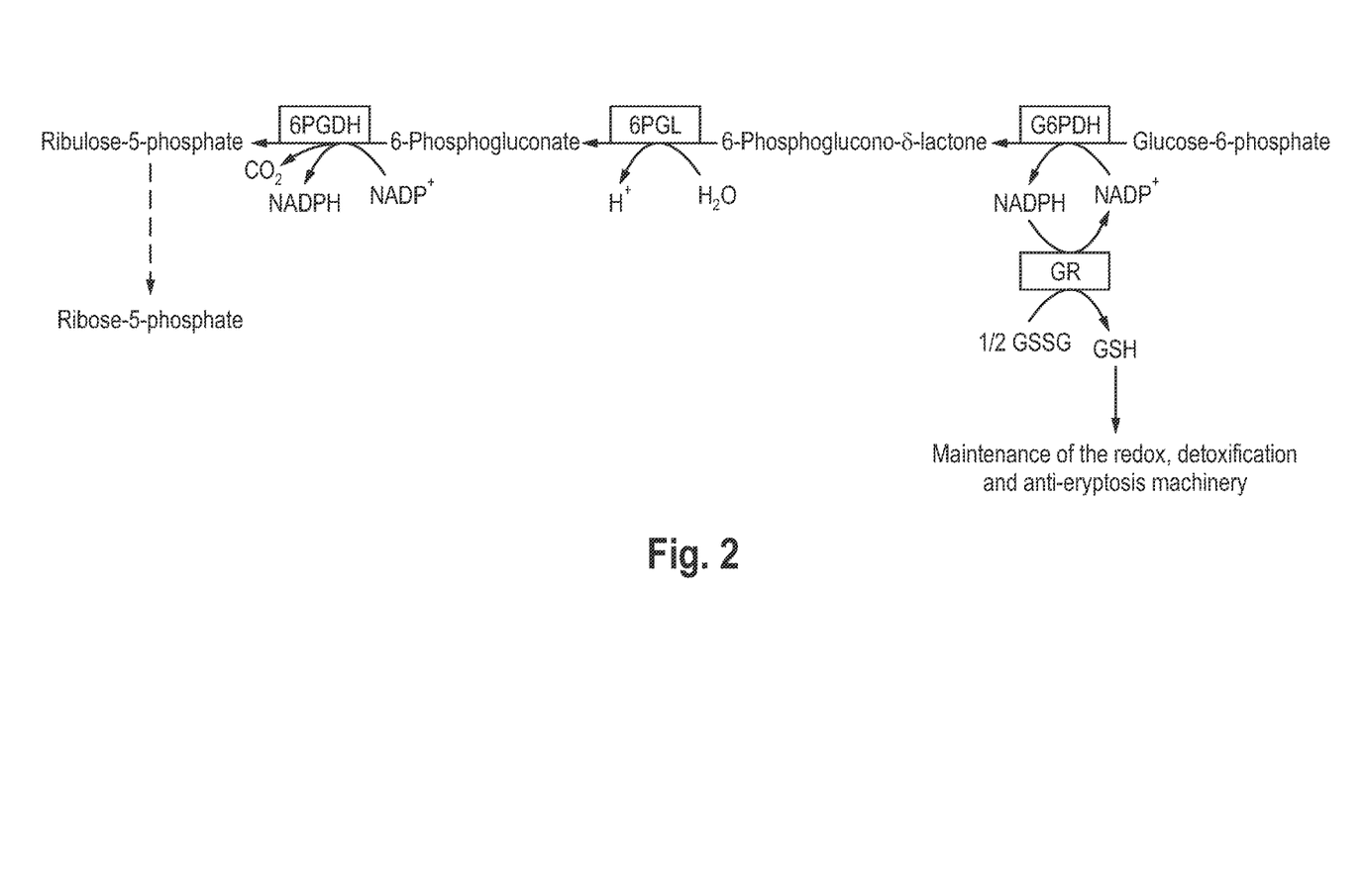
FIG. 2 presentation of the oxidative part of the pentose phosphate pathway (PPP) as the only source of the NADPH production in mature (non-nucleated), human erythrocytes.

2 GSH ⇌ GR ⇌ GSSG        GR   Glutathione reductase

The glucose-6-phosphate dehydrogenase (G6PDH) converts glucose-6-phosphate into 6 phosphoglucono-delta lactone resulting in the first NADPH molecule. The second NADPH molecule results from the conversion of 6-phosphogluconate into ribulose-5-phosphate mediated by the 6-phosphogluconate dehydrogenase (6PGDH). The resulting NADPH molecules serve by themselves as co-factors for the glutathione reductase (GR), which converts the oxidized form of the glutathione (GSSG) into the reduced form (GSH) (see FIG. 2; 6PGL: 6-phosphogluconolactonase).

The decisive point is that the newly regenerated GSH molecules by themselves are scavenged/depleted from the substances according to the invention by means of a conjugate. Finally, the intracellular concentration of the GSH and the GSSG molecules, depending on the used concentration of Bay 11-7082 or parthenolide or dimethylfumarate, respectively, increase massively or entirely; see Tables 1 and 2.

primary enzyme of the oxidative part of the pentose phosphate pathway (PPP) oxidizes its specific substrate, glucose-6-phosphate, resulting in the formation of the first NADPH molecule in mature human erythrocytes. The produced NADPH molecule serves, in turn, as a co-factor for the glutathione reductase (GR), which, as integral component of the antioxidant system converts its physiological substrate GSSG into GSH, with the result that erythrocytes are protected from the eryptosis (death of erythrocytes); see FIG. 2.

The inventor concluded that a GSSG depletion caused by Bay 11-7082 or parthenolide or dimethylfumarate, respectively, may have a direct influence on the activity of the NADPH-producing enzymes G6PDH, 6PGDH, and therefore on the activity of the NADPH-dependent flavoprotein, the glutathione reductase (GR).

For these reasons, further experiments were carried out while maintaining the same conditions as described for the

TABLE 2

Treatment of human erythrocytes with Bay 11-7082, parthenolide or dimethylfumarate is associated with a factual entire GSH depletion. Human erythrocytes (0.6% Hct) were treated for 24 hours in absence or presence of Bay 11-7082, parthenolide or dimethylfumarate. The erythrocytes treated with dimethyl sulfoxide (DMSO) served as negative control. Number of the independent experiments n = 3.

|  | DMSO | Bay 11-7082 (20 μM) | Parthenolide (50 μM) | Dimethylfumarate (140 μM) |
| --- | --- | --- | --- | --- |
| GSSG [nmol/mg Hemoglobin] | 7.52 | 0.00 | 0.30 | 0.17 |

2 GSH ⇌ GR ⇌ GSSG        GR   Glutathione reductase

Figure 3:
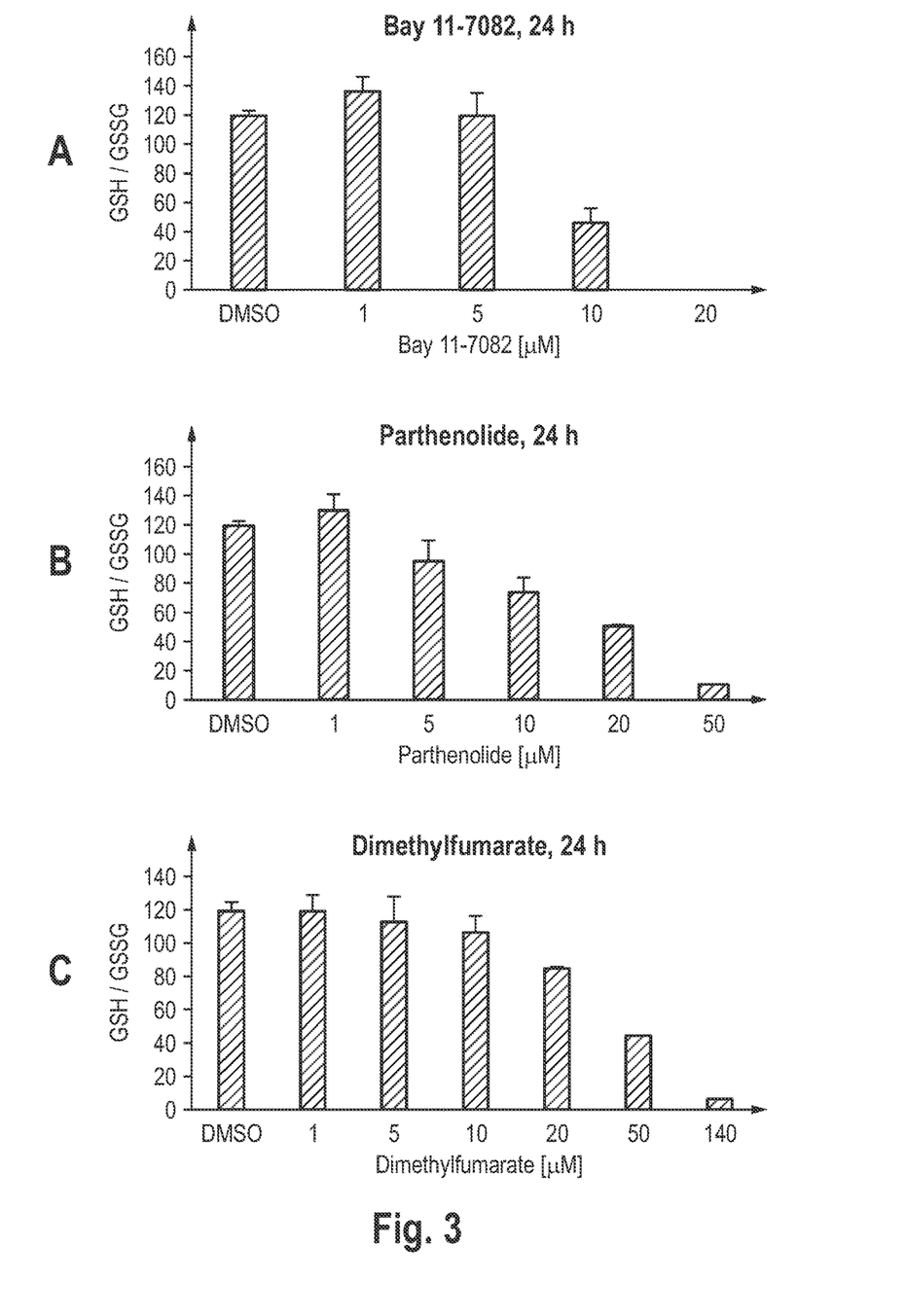
FIG. 3 concentration-dependent decrease of the GSH:GSSG ratio after the treatment of mature human erythrocytes with Bay 11-7082 or parthenolide or dimethylfumarate, GSSG is the oxidized form of the antioxidant glutathione.

In the FIG. 3 it is shown that the GSH:GSSG ratio in using 20 μM Bay 11-7082, 50 μM parthenolide or 140 μM dimethylfumarate is equal to 0 or is approaching 0.

In the underlying experiment human erythrocytes (0.6% hematocrit) were treated for 24 hours in absence or presence of Bay 11-7082, parthenolide or dimethylfumarate. These substances were solved in dimethyl sulfoxide (DMSO) and the DMSO-treated erythrocytes served as negative control. While the GSH:GSSG ratio in using 20 μM Bay 11-7082, 50 μM parthenolide or 140 μM dimethylfumarate is equal to 0 or approaching 0 the GSH:GSSG ratio in the DMSO-treated erythrocytes shows a ratio of 125:1. The experiment was in total carried out for three times with blood from three different individuals.

GSSG as oxidized form of the glutathione and as electron acceptor for the NADPH-depending glutathione reductase (GR) stimulates very effectively the activity of the glucose-6-phosphate dehydrogenase (G6PDH). The latter as the experiment from FIG. 1, to examine a potential influence of Bay 11-7082 or parthenolide or dimethylfumarate on the activities of the G6PDH, 6PGDH and GR. The results are definite. It could be reached a 100% G6PDH-inhibition with Bay 11-7082 at 20 μM or with parthenolide at 50 μM and an approximately ≥50% inhibition of G6PDH by dimethylfumarate at 140 μM; see FIG. 4a to c. The clinically relevant concentrations of Bay 11-7082 (20 mM) or parthenolide (50 μM) resulted in a complete inhibition of the G6PDH activity, while dimethylfumarate (140 μM) can cause an approximately ≥50% inhibition of G6PDH; see also FIG. 5. Human erythrocytes (0.6% hematocrit) were treated for 24 hours in absence or presence of Bay 11-7082, parthenolide or dimethylfumarate. The DMSO-treated erythrocytes served as negative control. The experiment was in total carried out for three times with blood from three different individuals.

The obtained data are of significant clinical importance. From now on the substances Bay 11-7082, parthenolide and dimethylfumarate can be considered directly for the treatment of obesity or adiposis and NADPH superoxide anion associated cardiovascular diseases.

The metabolism includes the sum of all chemical conversions in a cell or an organism. There are in total two glucose metabolizing pathways in the human organism, namely the catabolic, energy-producing pathway, and the anabolic biosynthesis pathway. G6PDH as the first enzyme of a biosynthesis pathway is involved, by the oxidation of its specific substrate, the glucose-6-phosphate, into the synthesis of the ribulose-5-phosphate (see FIG. 2) and, by simultaneous NADPH production, into the synthesis of the fatty acids and cholesterol. NADPH is an important compound of the lipogenesis.

Patients with a G6PDH deficiency show a reduced lipogenesis and a significant decrease of the lipoprotein concentration. Overweight persons show an enormous G6PDH expression and activity. Furthermore, a high G6PDH expression in the fat cells is tightly connected with a lipid dysregulation, oxidative stress and chronic inflammation in overweight and diabetic persons. In a headline style it can be said: "G6PDH converts glucose into fat".

The pro-oxidant enzymes, such as the NADPH-dependent oxidases (NOXs) and the nitrogen oxide synthase (NOS) with NADPH as a co-factor can convert molecular oxygen ($O_2$) into the superoxide anion ($O_2.^-$). This continuous increase of the formation of the superoxide anion in patients with cardiac insufficiency is very prominent due to the significant increase oxidation of the glucose-6-phosphate by G6PDH and the permanent amplification of the NADPH production associated therewith. This anomaly of the ($O_2.^-$) formation is an essential factor which significantly promotes inflammatory processes and oxidative stress in cardiac insufficient patients. This is one of the main reasons for the premature death of people suffering from a heart condition.

Figure 5:
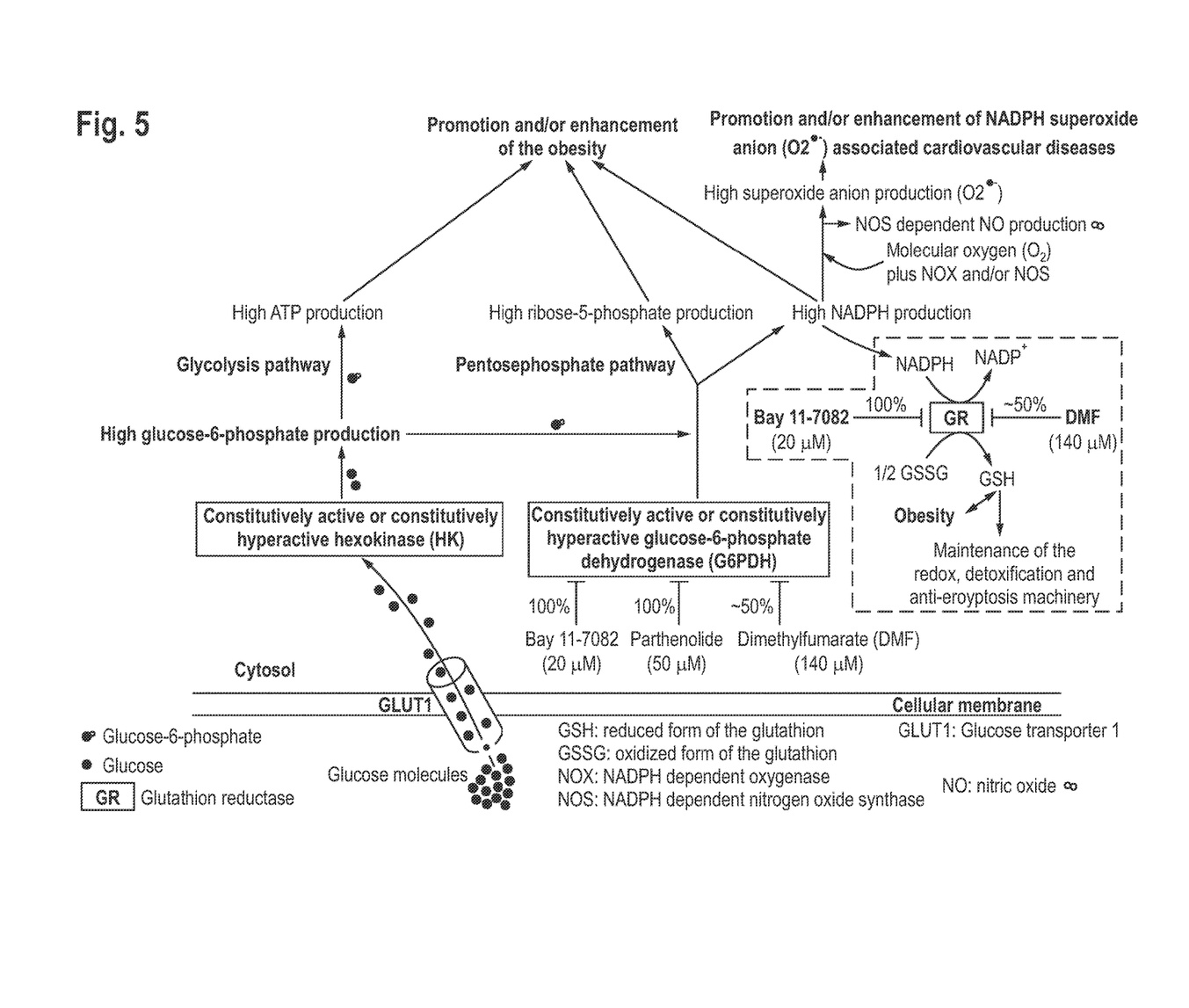
FIG. 5 direct contribution of the constitutively active or hyperactive glucose-6-phosphate dehydrogenase (G6PDH) in the promotion/amplification of obesity and NADPH superoxide anion ($O_2.^-$) associated cardiovascular diseases.

Against this background the degree of a development of obesity but also the intensity of the NADPH superoxide anion associated cardiovascular diseases can be controlled and strictly limited by a targeted and dosed inhibition of the enzymatic activity of the glucose-6-phosphate dehydrogenase with Bay 11-7082, parthenolide and/or dimethylfumarate; see FIG. 5.

In further experiments it could be shown for the first time that the pharmacological substances Bay 11-7082 and dimethylfumarate at clinically relevant concentrations can significantly inhibit the activity of the glutathione reductase (GR) in mature (non-nucleated) human erythrocytes. The result of this experiment is shown in the FIG. 6.

Figure 6:
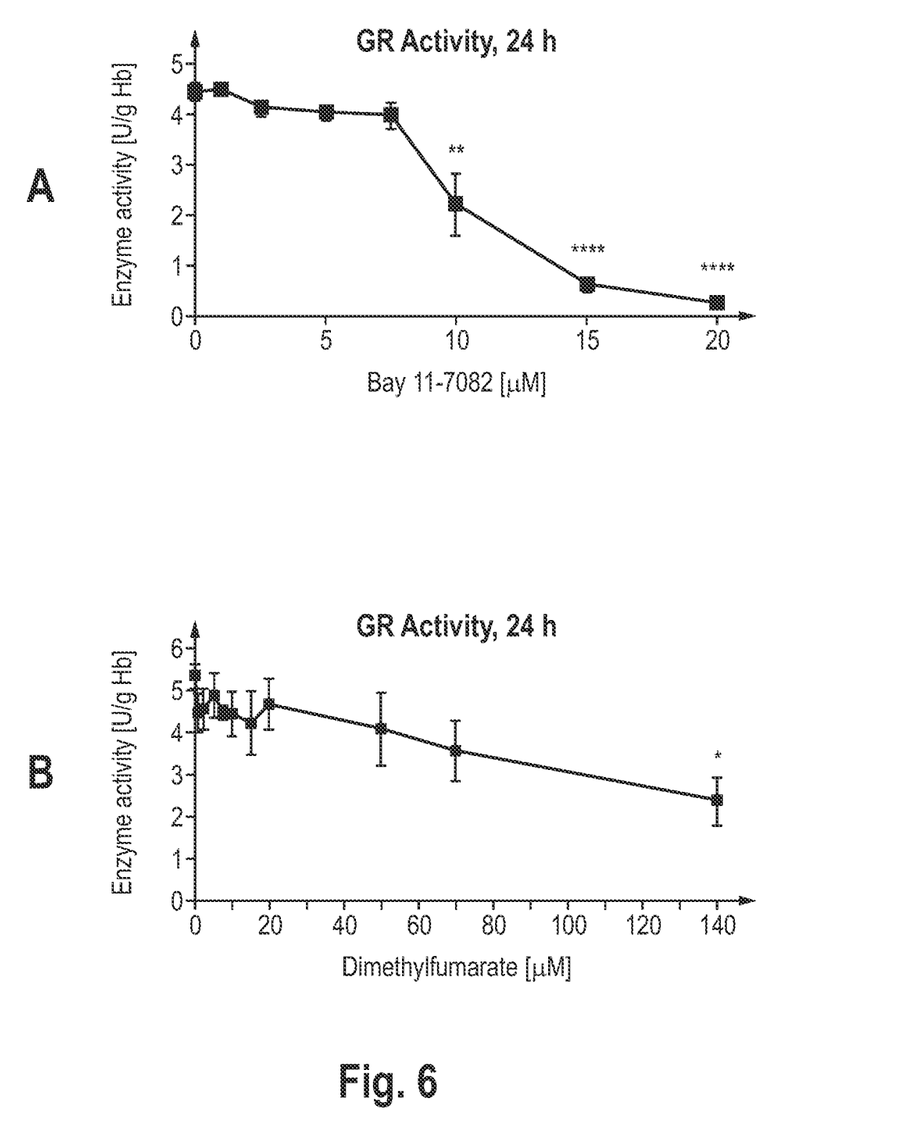
FIG. 6 inhibitory effect of Bay 11-7082 and dimethylfumarate on the activity of the glutathione reductase (GR)

While Bay 11-7082 (20 µM) causes a complete GSR inhibition, the clinically relevant dimethylfumarate concentration (140 µM) can result in an approximately ≥50% GR inhibition. Human erythrocytes (0.6% Hct) were treated for 24 hours in the absence or presence of Bay 11-7082, parthenolide or dimethylfumarate, the DMSO-treated erythrocytes served as negative control. The experiment was in total carried out for three times with blood from three different individuals.

The NADPH-dependent GSR is directly involved in the regeneration of the reduced form of the glutathione (GSH); see FIG. 5. It is known that the GSH level in fatty tissue of mice with obesity is much higher than in sibling mice without obesity. It is also known that the decrease of GSH caused by L-BSO (L-buthionine-(S,R)-sulfoxymine) prevents in vivo obesity induced by diet.

Figure 4:
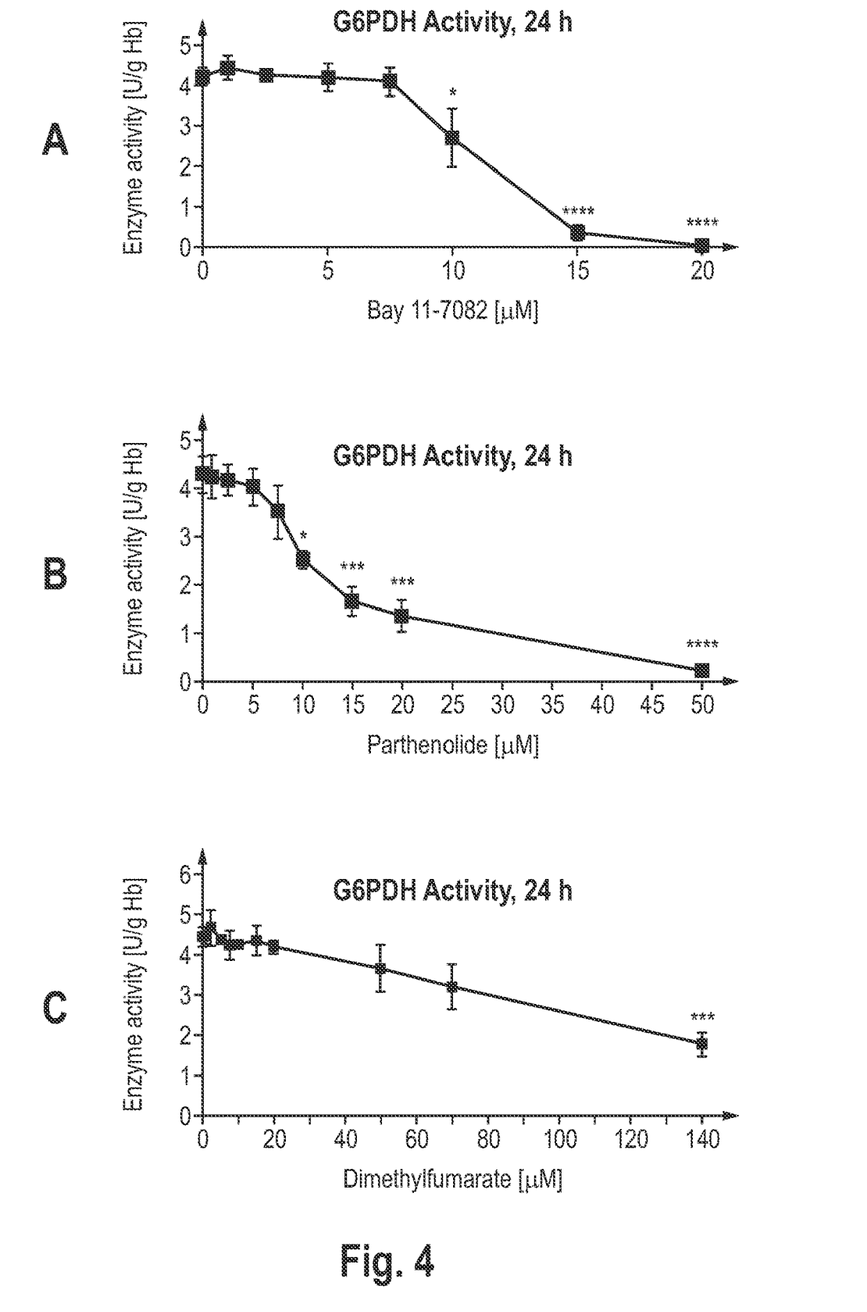
FIG. 4 presentation of the concentration-dependent influence of Bay 11-7082, parthenolide, and dimethylfumarate on the G6PDH activity.

The results shown in the FIGS. 4 and 6 stress the versatility of the substances according to the invention which are in a position to significantly inhibit the activity of the lipogenic enzyme G6PDH and the activity of the GSH regenerating enzyme (GR). These substances can, therefore, play a prominent role in the treatment and prophylaxis of the obesity and also the NADPH superoxide anion associated cardiovascular disease; see FIG. 5.

The findings according to the invention and the obtained data provide far beyond the erythrocyte research the basis, also in nucleated cells, to treat a number of diseases, in particular adipositas and NADPH superoxide anion associated cardiovascular diseases by controlled and effective inhibition of the activity of the glucose-6-phosphate dehydrogenase (G6PDH); see FIG. 5.

Figure 7:
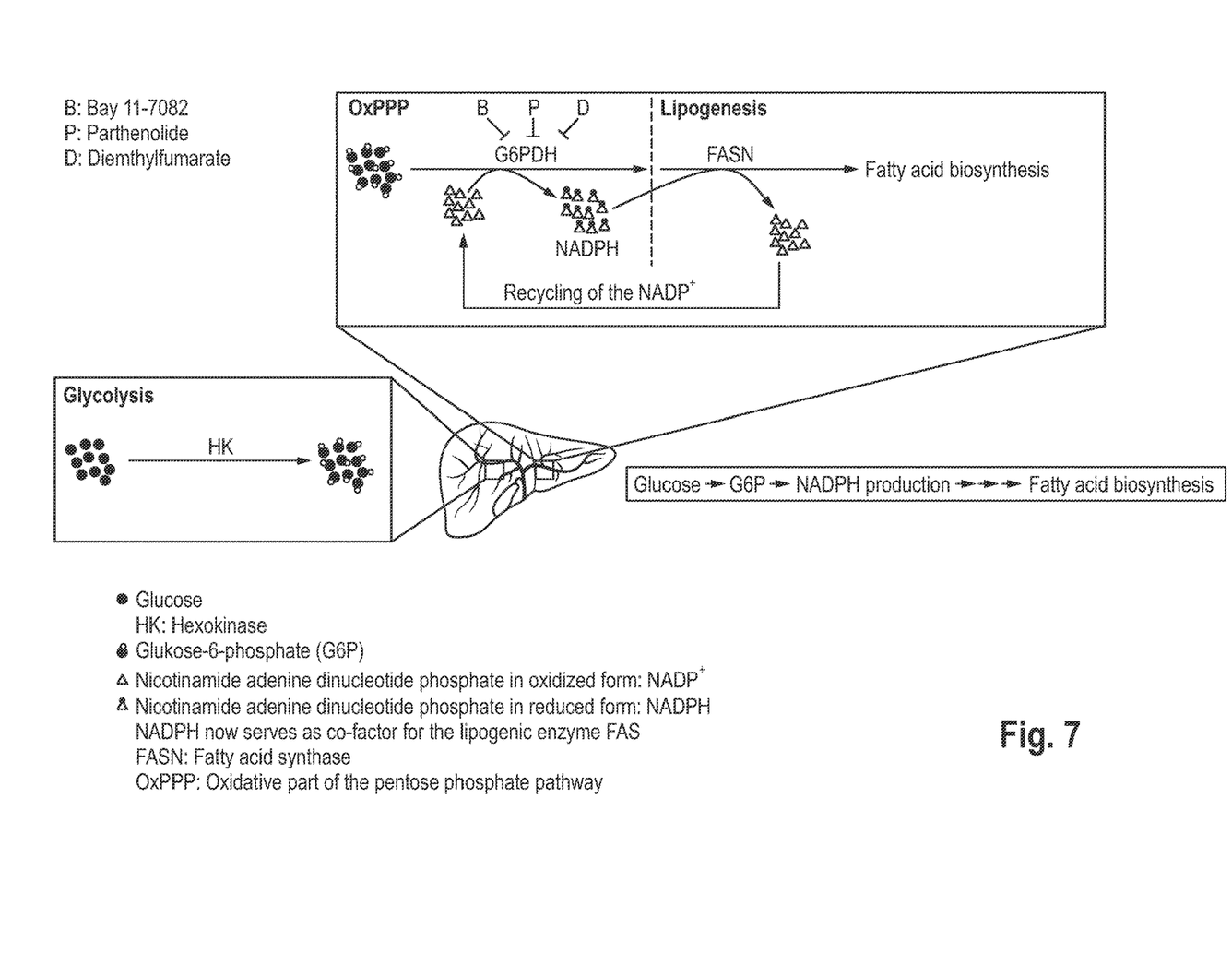
FIG. 7 glucose-6-phosphate dehydrogenase (G6PDH) dependent NADPH production and its absolute necessity for the fatty acid biosynthesis in mammals.

In view of a use of the invention in obesity in FIG. 7 it is illustrated that the glucose-6-phosphate dehydrogenase (G6PDH)-dependent NADPH production is absolutely necessary for the fatty acid biosynthesis in mammals. There exists four enzymes which produce the co-factor NADPH. They are: G6PDH, 6-phosphogluconate dehydrogenase (6PGDH), isocitrate dehydrogenase (ICDH) and malic enzyme (ME). The enzyme G6PDH is the most important enzyme in this group and has the major share in the NADPH production. The NADPH-dependent and lipogenic enzyme fatty acid synthase (FASN) then starts with the fatty acid biosynthesis (simplified illustration). The pharmacological substances Bay 11-7082, parthenolide and dimethylfumarate (see above) can downregulate the fatty acid biosynthesis by G6PDH-inhibition (see Ghashghaeinia et al. 2016; Sci Rep. 6: 28754. doi: 10.1038/srep28754) and, in doing so, considered for the treatment of obesity.

The present invention provides an entirely new, clinically relevant application for the pharmacological substances Bay 11-7082, parthenolide and dimethylfumarate. Glucose-6-phosphate dehydrogenase (G6PDH) as lipogenic, NADPH-producing and first enzyme of the biosynthesis pathway plays a central role in numerous biological processes, such as cell growth, development, progression of diseases, senescence and cell death. Due to their inhibitory effect on the G6PDH activity or GR activity the substances according to the invention Bay 11-7082, pathenolide and dimethylfumarate have the potential to effectively treat or prevent obesity and NADPH superoxide anion associated cardiovascular diseases.

What is claimed is:

1. A method for the prophylaxis or treatment of obesity, comprising administering into a living being in need at least one active agent selected from the group consisting of Bay 11-7082 and parthenolide.

2. The method of claim 1, wherein administration of the at least one active agent causes an inhibition of the glucose-6-phosphate dehydrogenase (G6PDH) in the living being.

3. The method of claim 1, comprising administering the at least one active agent in such a concentration that in vivo an inhibition of the G6PDH is reached by ≥50%.

4. The method of claim 1, comprising administering the at least one active agent in such a concentration that in vivo the following concentration is achieved:
   approximately ≥20 µM Bay 11-7082, or
   approximately ≥50 µM parthenolide.

5. The method of claim 1, wherein administration of the at least one active agent results in an inhibition of the glutathione reductase (GR).

6. The method of claim 5, comprising administering the at least one active agent in such a concentration that in vivo an inhibition of the GR is achieved by ≥50%.

7. The method of claim 1, comprising administering an additional active agent, wherein said additional active agent is effective against obesity.

8. A method for the prophylaxis or treatment of obesity, comprising administering into a living being in need at least one active agent selected from the group consisting of Bay 11-7082 and parthenolide.

* * * * *